US012427647B2

(12) United States Patent
Kokushi et al.

(10) Patent No.: US 12,427,647 B2
(45) Date of Patent: Sep. 30, 2025

(54) ROBOT SYSTEM (71) Applicant: KAWASAKI JUKOGYO KABUSHIKI KAISHA, Kobe (JP)

(72) Inventors: Hiroki Kokushi, Kobe (JP); Hideyuki Ryu, Kobe (JP)

(73) Assignee: KAWASAKI JUKOGYO KABUSHIKI KAISHA, Kobe (JP)

(*) Notice: Subject to any disclaimer, the term of this patent is extended or adjusted under 35 U.S.C. 154(b) by 146 days.

(21) Appl. No.: 18/557,072

(22) PCT Filed: Apr. 25, 2022

(86) PCT No.: PCT/JP2022/018746
§ 371 (c)(1),
(2) Date: Oct. 25, 2023

(87) PCT Pub. No.: WO2022/230815
PCT Pub. Date: Nov. 3, 2022

(65) Prior Publication Data
US 2024/0217089 A1  Jul. 4, 2024

(30) Foreign Application Priority Data
Apr. 27, 2021  (JP) ................. 2021-075077

(51) Int. Cl.
B25J 3/00 (2006.01)
A61B 10/00 (2006.01)
B25J 9/00 (2006.01)

(52) U.S. Cl.
CPC ............ B25J 3/00 (2013.01); A61B 10/0051 (2013.01); B25J 9/0084 (2013.01)

(58) Field of Classification Search
CPC ............... B25J 3/00; B25J 9/00; B25J 9/0084
USPC .................................. 700/245, 248; 600/582
See application file for complete search history.

(56) References Cited

U.S. PATENT DOCUMENTS

| | | | | |
|---|---|---|---|---|
| 8,600,551 | B2* | 12/2013 | Itkowitz | A61B 34/77 700/250 |
| 9,314,922 | B2* | 4/2016 | Dockter | B25J 9/1689 |
| 10,022,871 | B2* | 7/2018 | Ogawa | A61B 34/74 |
| 10,551,923 | B2* | 2/2020 | Pirasmepulkul | G06F 3/011 |
| 11,844,585 | B1* | 12/2023 | Friedrich | A61B 34/37 |
| 11,974,731 | B2* | 5/2024 | Sun | A61B 10/0051 |
| 2004/0254680 | A1* | 12/2004 | Sunaoshi | A61B 34/37 700/253 |
| 2009/0248200 | A1* | 10/2009 | Root | B25J 9/1602 700/245 |
| 2012/0041599 | A1* | 2/2012 | Townsend | B25J 9/1689 700/275 |

(Continued)

FOREIGN PATENT DOCUMENTS

| | | |
|---|---|---|
| JP | H8-275958 A | 10/1996 |
| JP | 3228999 U | 11/2020 |
| WO | 2016/125385 A1 | 8/2016 |

Primary Examiner — Khoi H Tran
(74) Attorney, Agent, or Firm — METROLEX IP LAW GROUP, PLLC; Robert L. Scott, Esq.

(57) ABSTRACT

A robot system includes a master robot, a plurality of slave robots remotely controlled by the master robot to perform a procedure on a person to be treated, and a switching controller configured or programmed to switch an operational connection between the master robot and each of the plurality of slave robots such that one of the plurality of slave robots is remotely controlled by the master robot.

5 Claims, 8 Drawing Sheets

(56) References Cited

U.S. PATENT DOCUMENTS

| | | | |
|---|---|---|---|
| 2016/0128790 A1* | 5/2016 | Ogawa | B25J 9/1689 |
| | | | 606/130 |
| 2017/0333143 A1 | 11/2017 | Yoshii | |
| 2018/0243920 A1* | 8/2018 | Hashimoto | B25J 9/1697 |
| 2019/0314097 A1* | 10/2019 | Diolaiti | A61B 34/37 |
| 2022/0118615 A1* | 4/2022 | Yajima | A61B 34/37 |

* cited by examiner

ROBOT SYSTEM

TECHNICAL FIELD

The present disclosure relates to a robot system, and more particularly, it relates to a robot system that performs a procedure such as collecting a specimen from a person to be treated.

BACKGROUND ART

Conventionally, a specimen collection box for collecting a specimen from a person to be treated is known (see Patent Document 1, for example). Patent Document 1 discloses a specimen collection box including a specimen collection main body box and a pair of protective gloves provided on the specimen collection main body box. In this specimen collection box, an operation person who collects a specimen is placed in the specimen collection main body box and collects the specimen from a person to be treated through the pair of protective gloves.

PRIOR ART

Patent Document

Patent Document 1: Japanese Utility Model Registration No. 3228999

SUMMARY OF THE INVENTION

Problem to be Solved by the Invention

However, in the technology described in Patent Document 1, the operation person is placed in the specimen collection main body box and collects the specimen from the person to be treated through the pair of protective gloves, and thus the operation person needs to be positioned close to the person to be treated. Furthermore, the operation person is placed in the specimen collection main body box, and thus it is necessary to take air into the specimen collection main body box. Therefore, the operation person has a high risk of being infected when collecting the specimen from the person to be treated.

The present disclosure is intended to solve the above problem. The present disclosure aims to provide a robot system capable of reducing the risk of infection from a person to be treated to an operation person.

Means for Solving the Problem

In order to attain the aforementioned object, a robot system according to an aspect includes a master robot, a plurality of slave robots remotely controlled by the master robot to perform a procedure on a person to be treated, and a switching controller configured or programmed to switch an operational connection between the master robot and each of the plurality of slave robots such that one of the plurality of slave robots is remotely controlled by the master robot. The term "to perform a procedure on a person to be treated" in the present disclosure indicates a broader concept including not only collecting a specimen from the person to be treated but also performing an examination on the person to be treated, etc.

As described above, the robot system according to this aspect includes the master robot and the plurality of slave robots remotely controlled by the master robot to perform the procedure on the person to be treated. Accordingly, an operation person who operates the master robot does not need to be positioned close to the person to be treated, and thus the risk of infection to the operation person can be reduced when the procedure is performed on the person to be treated. Furthermore, the plurality of slave robots can be remotely controlled by one master robot while the plurality of slave robots are switched, and thus after the procedure is performed on the person to be treated by one slave robot, the procedure can be performed on another person to be treated using another slave robot while a booth in which the procedure has been performed is disinfected to prevent infection or while a person to be treated is on standby in the booth. Consequently, the number of procedures performed per unit time can be increased. Furthermore, it is not necessary to provide a master robot for each slave robot, and thus the number of master robots provided can be reduced. Thus, the system configuration can be simplified, and an increase in the size of the installation space can be reduced or prevented.

Effect of the Invention

As described above, the risk of infection from the person to be treated to the operation person can be reduced.

MODES FOR CARRYING OUT THE INVENTION

The configuration of a robot system 100 according to an embodiment is now described with reference to FIGS. 1 to 9.

Figure 1:
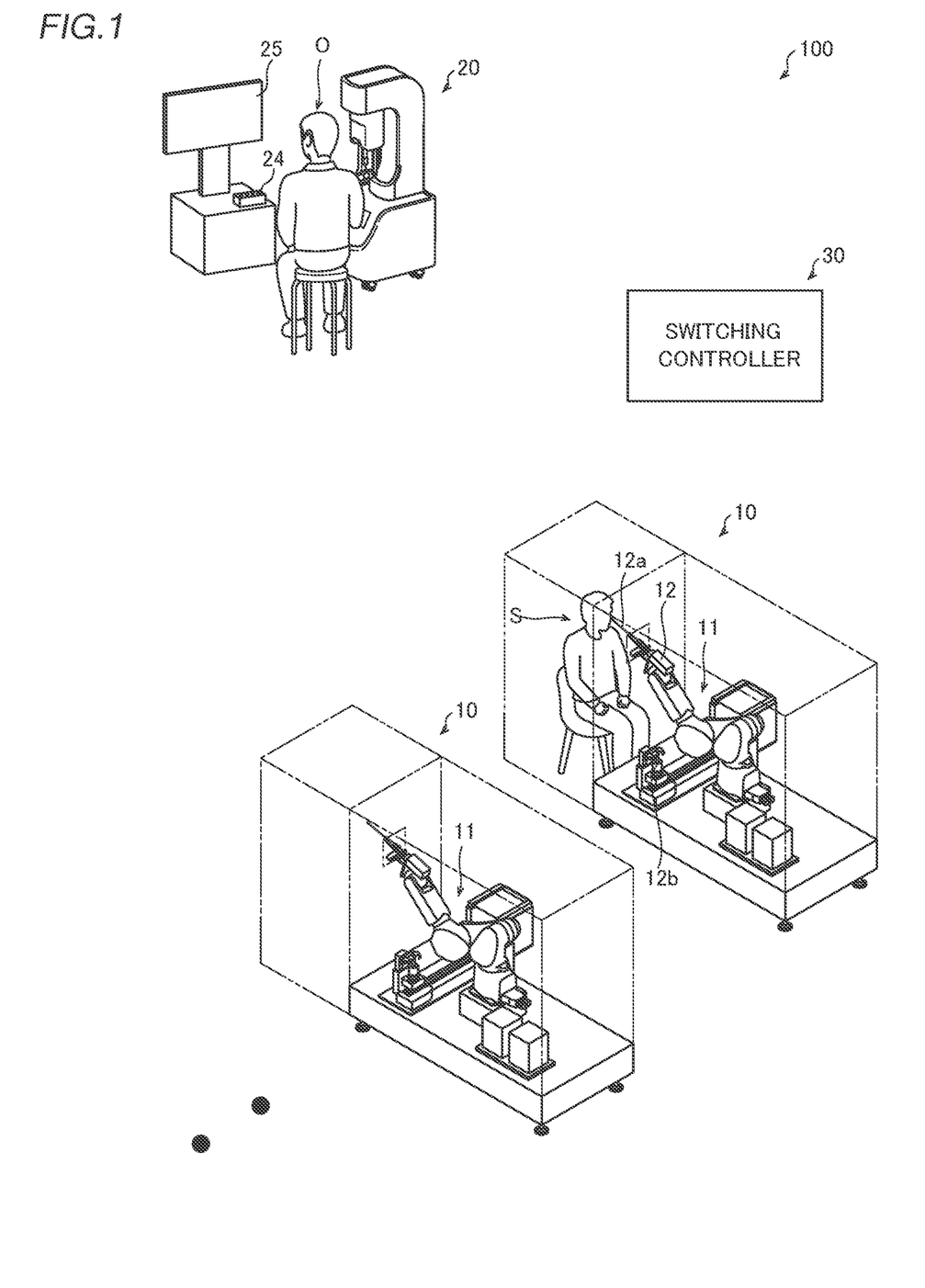
FIG. 1 is a diagram schematically showing a robot system according to an embodiment.

As shown in FIG. 1, the robot system 100 is provided to collect a specimen from a subject S. The robot system 100 includes a plurality of booths 10, a plurality of slave robots 11, a master robot 20, and a switching controller 30. The subject S is an example of a "person to be treated" in the claims.

In the booths 10, a specimen is collected from the subject S by the slave robots 11. The booths 10 are covered with walls on their sides. The slave robots 11 are arranged in the plurality of booths 10, respectively. Areas of the booths 10 in which the slave robots 11 are arranged are separated from areas into which the subject S enters by partition walls.

Figure 6:
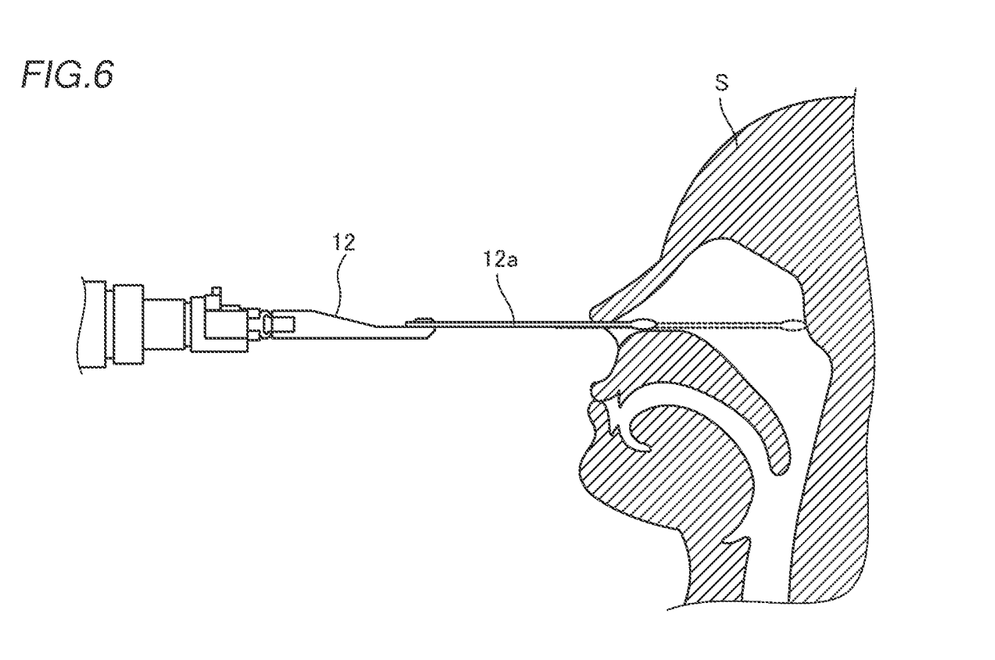
FIG. 6 is a diagram for illustrating specimen collection of the robot system according to the embodiment.

Each of the slave robots 11 is remotely controlled by the master robot 20 to collect a specimen from the subject S. The slave robot 11 collects a specimen from the subject S using a specimen collection member 12*a*. The specimen collection member 12*a* is a sterile swab, for example. The sterile swab has a stick shape. The slave robot 11 inserts the specimen collection member 12*a* into the nasal cavity of the subject S, for example, and collects the specimen (nasopharyngeal swab) from the nasopharynx of the subject S by the inserted specimen collection member 12*a*, as shown in FIG. 6. The slave robot 11 may insert the specimen collection member 12*a* into the oral cavity of the subject S to collect the specimen. A virus test such as a PCR (polymerase chain reaction) test is performed on the collected specimen.

Figure 2:
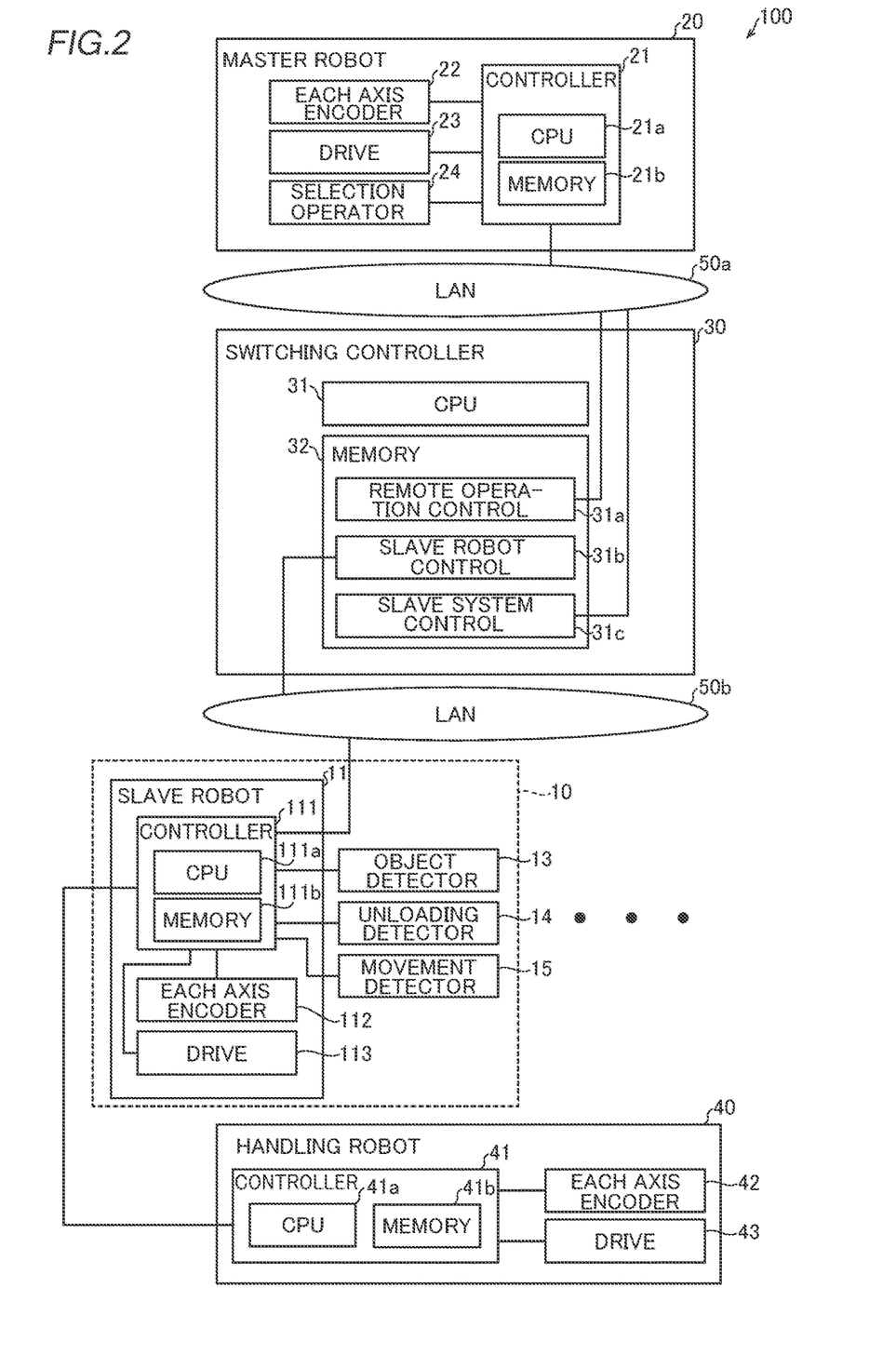
FIG. 2 is a block diagram showing the control configuration of the robot system according to the embodiment.

The slave robot 11 includes a vertical articulated robot. A hand 12 is provided on a tip end of the slave robot 11. The slave robot 11 has a plurality of (seven, for example) joints. As shown in FIG. 2, each of the plurality of joints of the slave robot 11 includes a drive 113 such as a servomotor, and an encoder 112 that detects the driving position of the drive 113. The hand 12 can hold the specimen collection member 12*a*. The hand 12 includes a pair of gripping members, for example, and can grip and hold the specimen collection member 12*a* with the pair of gripping members.

The slave robot 11 includes a controller 111 that controls movement of the slave robot 11. The controller 111 includes a central processing unit (CPU) 111*a* and a memory 111*b*. The CPU 111*a* controls movement of the slave robot 11 based on a program stored in the memory 111*b*.

The slave robot 11 is moved in a direction corresponding to a direction in which an operation person O operates the master robot 20. For example, when the operation person O moves the master robot 20 in an upward-downward direction (Z direction), the hand 12 of the slave robot 11 (and the specimen collection member 12*a* held by the hand 12) is moved in the upward-downward direction. When the operation person O moves the master robot 20 in a right-left direction (Y direction), the hand 12 of the slave robot 11 (and the specimen collection member 12*a* held by the hand 12) is moved in the right-left direction. When the operation person O moves the master robot 20 in a forward-rearward direction (X direction), the hand 12 of the slave robot 11 (and the specimen collection member 12*a* held by the hand 12) is moved in the forward-rearward direction. When a specimen is collected from the subject S using the specimen collection member 12*a*, the operation person O moves the master robot 20 in a forward direction (X1 direction) to move the hand 12 of the slave robot 11 (and the specimen collection member 12*a* held by the hand 12) in the forward direction (insertion direction) such that the specimen collection member 12*a* is inserted into the nasal cavity of the subject S.

As shown in FIG. 1, the master robot 20 remotely controls the slave robot 11. Specifically, the master robot 20 remotely controls the slave robot 11 by being operated by the operation person O such as a doctor. The master robot 20 outputs an operation signal based on an operation of the operation person O. The slave robot 11 performs an action corresponding to the operation of the operation person O based on the operation signal from the master robot 20. The slave robot 11 and the master robot 20 are communicably connected to each other by wire or wirelessly.

As shown in FIG. 2, the master robot 20 includes a controller 21, an encoder 22, a drive 23, and a selection operator 24. Furthermore, as shown in FIG. 1, the master robot 20 includes a display 25.

The controller 21 controls the master robot 20 and acquires an operation on the master robot 20 by the operation person O. The controller 21 includes a CPU 21*a* and a memory 21*b*. The CPU 21*a* controls the master robot 20 based on a program stored in the memory 21*b*.

The encoder 22 detects the driving position of the drive 113 such as a servomotor. The drive 23 drives each joint of the master robot 20.

The selection operator 24 is provided to select a slave robot 11 to be remotely controlled by the master robot 20 from among the plurality of (four) slave robots 11. That is, the selection operator 24 receives an operation of the operation person O to select the slave robot 11.

The master robot 20 is communicably connected to the switching controller 30 via a LAN (local area network) 50*a*. Furthermore, the switching controller 30 is communicably connected to each of the plurality of slave robots 11 via a LAN 50*b*.

The display 25 displays an image (video) of the subject S. The display 25 displays a video captured by a camera (not shown) provided at the tip end of the slave robot 11 to image the subject S from the front, and a video captured by a camera (not shown) that images the subject S from the side, for example. While checking the real-time video of the subject S displayed on the display 25, the operation person O remotely controls the slave robot 10 using the master robot 20. The display 25 includes a liquid crystal monitor, for example.

In this embodiment, the switching controller 30 switches an operational connection between the master robot 20 and each of the plurality of slave robots 11 such that one of the plurality of slave robots 11 is remotely controlled by the master robot 20.

The switching controller 30 includes a CPU 31 and a memory 32. The CPU 31 performs a control based on a program stored in the memory 32. The memory 32 stores a remote operation control 31*a*, a slave robot control 31*b*, and a slave system control 31*c* as software. The remote operation control 31*a* is connected to the master robot 20, and generates a movement command signal for moving the slave robot 11 based on an operation on the master robot 20. The slave robot control 31*b* is connected to the slave robot 11, and transmits the movement command signal generated by the remote operation control 31*a* to the slave robot 11 to be remotely controlled. The slave system control 31*c* is connected to the master robot 20, and performs a control to switch to the slave robot 11 to be remotely controlled by the master robot 20 and make an operational connection to the slave robot 11.

The switching controller 30 receives an operation signal for performing a remote control from the master robot 20, and transmits a movement command signal based on the operation signal to the slave robot 11 to be remotely controlled.

The switching controller 30 acquires whether or not the slave robot 11 selected by the selection operator 24 is moving, and when the selected slave robot 11 is stopped, the operational connection is switched such that the selected slave robot 11 is remotely controlled by the master robot 20.

Figure 5:
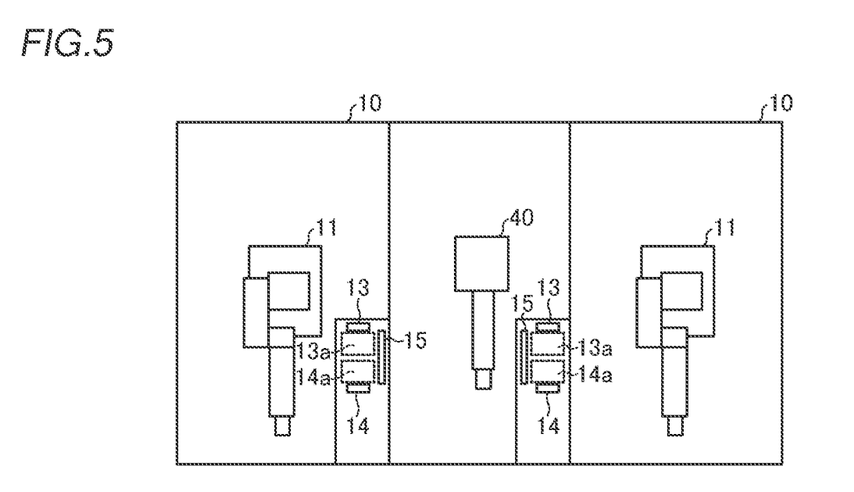
FIG. 5 is a diagram showing a handling robot of the second operation example of the robot system according to the embodiment.

On the slave robot 11 side, an object detector 13 is provided to detect that an object including the specimen collection member 12a for collecting a specimen and a specimen container 12b in which the specimen is to be stored has been placed at a supply position 13a at which the object is supplied to the slave robot 11, as shown in FIG. 5. Furthermore, on the slave robot 11 side, an unloading detector 14 is provided to detect that the specimen container 12b in which the collected specimen has been stored has been placed at an unloading position 14a. The supply position 13a is an example of a "predetermined position" in the claims.

When the object detector 13 detects that the object has been supplied to the supply position 13a, the slave robot 11 is remotely controlled for specimen collection. Furthermore, when the unloading detector 14 detects that the specimen container 12b has been unloaded from the unloading position 14a, the slave robot 11 is remotely controlled for specimen collection.

Figure 3:
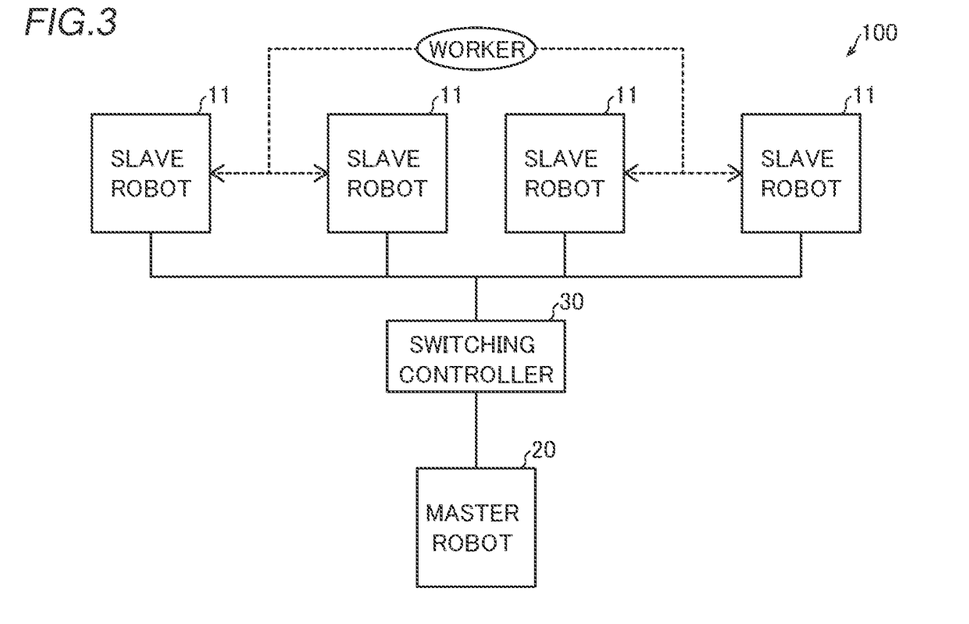
FIG. 3 is a diagram showing a first operation example of the robot system according to the embodiment.
Figure 4:
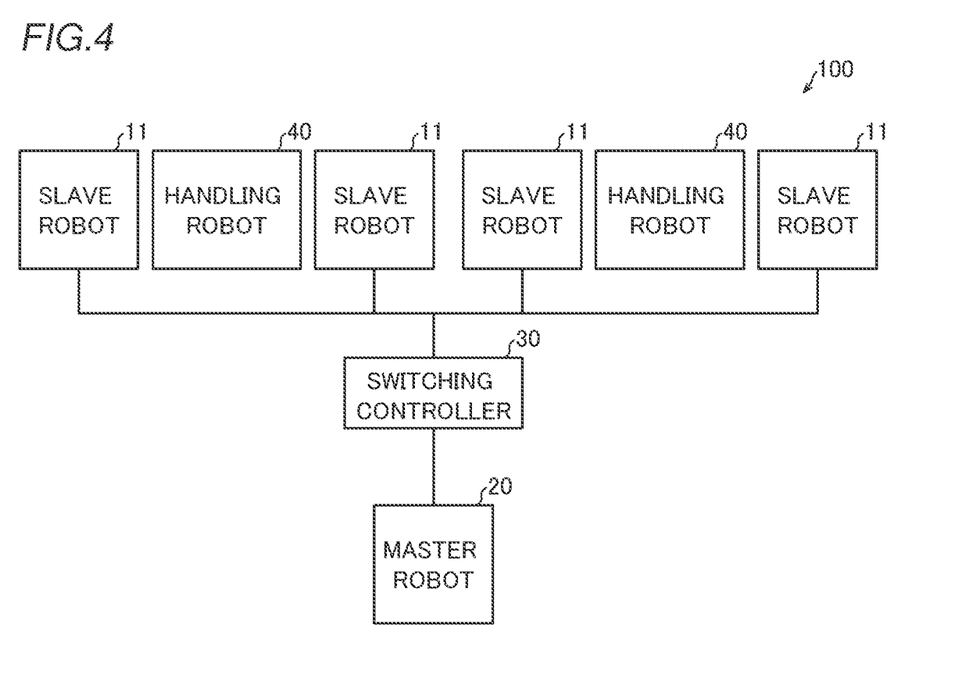
FIG. 4 is a diagram showing a second operation example of the robot system according to the embodiment.

The robot system 100 can switch the operation between manual operation shown in FIG. 3 and handling system operation shown in FIG. 4. In the manual operation, as shown in FIG. 3, a worker supplies the specimen collection member 12a and the specimen container 12b to the supply position 13a of the slave robot 11, and unloads the specimen container 12b into which the specimen has been collected. On the other hand, in the handling system operation, as shown in FIG. 4, in place of the worker, handling robots 40 supply the specimen collection members 12a and the specimen containers 12b to the supply positions 13a of the slave robots 11, and unload the specimen containers 12b into which the specimens have been collected.

In the robot system 100, the control of the slave robot 11 is common between the manual operation and the handling system operation, and the operation can be switched without changing the mechanical configuration and control configuration to move the slave robot 11.

As shown in FIG. 4, when the handling robots 40 are provided, each of the handling robots 40 supplies the object (the specimen collection member 12a and the specimen container 12b) to the supply position 13a, and unloads the specimen container 12b in which the collected specimen has been stored from the unloading position 14a. Furthermore, the handling robot 40 acquires the position of the slave robot 11 to supply the object (the specimen collection member 12a and the specimen container 12b) and unload the specimen container 12b. The handling robot 40 supplies the object (the specimen collection member 12a and the specimen container 12b) to the supply position 13a when the slave robot 11 is not located at the supply position 13a. The handling robot 40 unloads the specimen container 12b from the unloading position 14a when the slave robot 11 is not located at the unloading position 14a.

As shown in FIG. 5, a movement detector 15 is provided on the slave robot 11 side to detect movement of the handling robot 40 to the supply position 13a and the unloading position 14a. When the movement detector 15 does not detect the handling robot 40, the slave robot 11 acquires the object (the specimen collection member 12a and the specimen container 12b) from the supply position 13a. Furthermore, when the movement detector 15 does not detect the handling robot 40, the slave robot 11 places the specimen container 12b at the unloading position 14a.

The handling robot 40 includes a vertical articulated robot having a plurality of joints. The handling robot 40 transfers the specimen container 12b unloaded from the unloading position 14a to a subsequent process.

As shown in FIG. 4, the handling robot 40 is provided in common for the plurality of slave robots 11. For example, as shown in FIGS. 4 and 5, the handling robot 40 is arranged between two slave robots 11 and is provided in common for the two slave robots 11.

Specimen Collection Process

Figure 7:
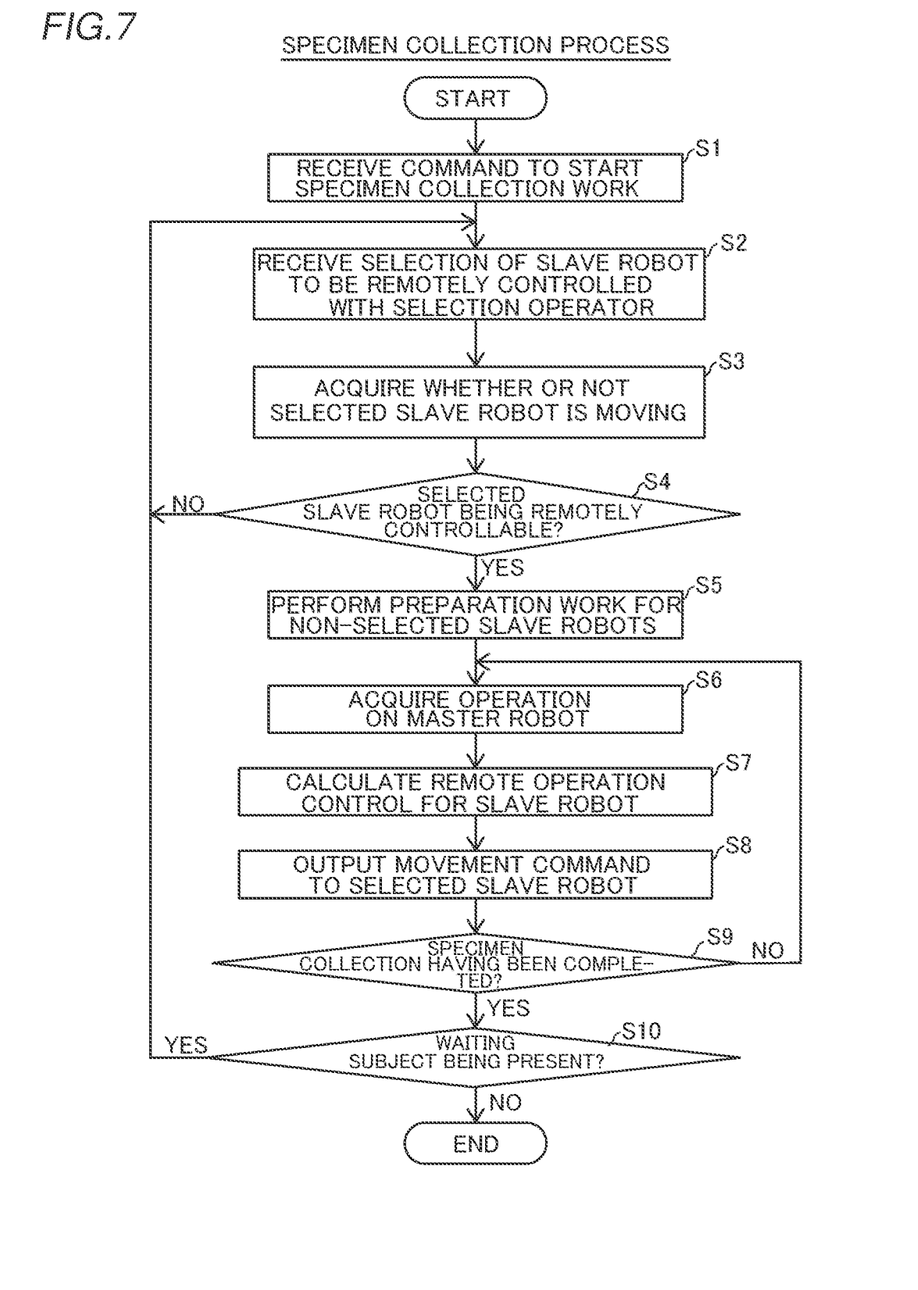
FIG. 7 is a flowchart for illustrating a specimen collection process of the robot system according to the embodiment.

A specimen collection process by the robot system 100 is now described with reference to FIG. 7.

In step S1, the controller 21 of the master robot 20 receives, from the operation person O, a command to start specimen collection work. In step S2, the controller 21 receives a selection of the slave robot 11 to be remotely controlled with the selection operator 24.

In step S3, the switching controller 30 acquires whether or not the selected slave robot 11 is currently moving. That is, the switching controller 30 acquires whether the selected slave robot 11 is moving for pre-processing or post-processing, or the selected slave robot 11 is waiting. In step S4, the switching controller 30 determines whether or not the selected slave robot 11 is remotely controllable. That is, the switching controller 30 determines that the selected slave robot 11 is not remotely controllable when the selected slave robot 11 is moving for pre-processing or post-processing. When the selected slave robot 11 is waiting, the switching controller 30 determines that the selected slave robot 11 is remotely controllable. When the selected slave robot 11 is remotely controllable, the process advances to step S5, and when the selected slave robot 11 is not remotely controllable, the process returns to step S2.

In step S5, preparation work for the non-selected slave robots 11 is performed. In step S6, the controller 21 of the master robot 20 acquires an operation on the master robot 20 from the operation person O. Then, the controller 21 transmits an operation signal based on the acquired operation to the switching controller 30.

In step S7, the switching controller 30 calculates a remote operation control for the slave robot 11 based on the operation signal received from the master robot 20. In step S8, the switching controller 30 outputs a movement command to the selected slave robot 11 based on the calculated remote operation control.

In step S9, the switching controller 30 determines whether or not specimen collection has been completed. Specifically, the switching controller 30 determines whether or not the operation person O has performed an operation to complete the specimen collection. When the specimen collection has been completed, the process advances to step S10, and when the specimen collection has not been completed, the process returns to step S6. In step S10, the switching controller 30 determines whether or not there is a waiting subject. When there is a waiting subject, the process returns to step S2, a target to be remotely controlled is switched to another slave robot 11, and the specimen collection process is performed on the waiting subject. When there is no waiting subject, the specimen collection process is terminated.

Specimen Collection Process Procedure

The procedure of the specimen collection process by the robot system 100 is now described with reference to FIGS. 8 and 9.

Figure 8:
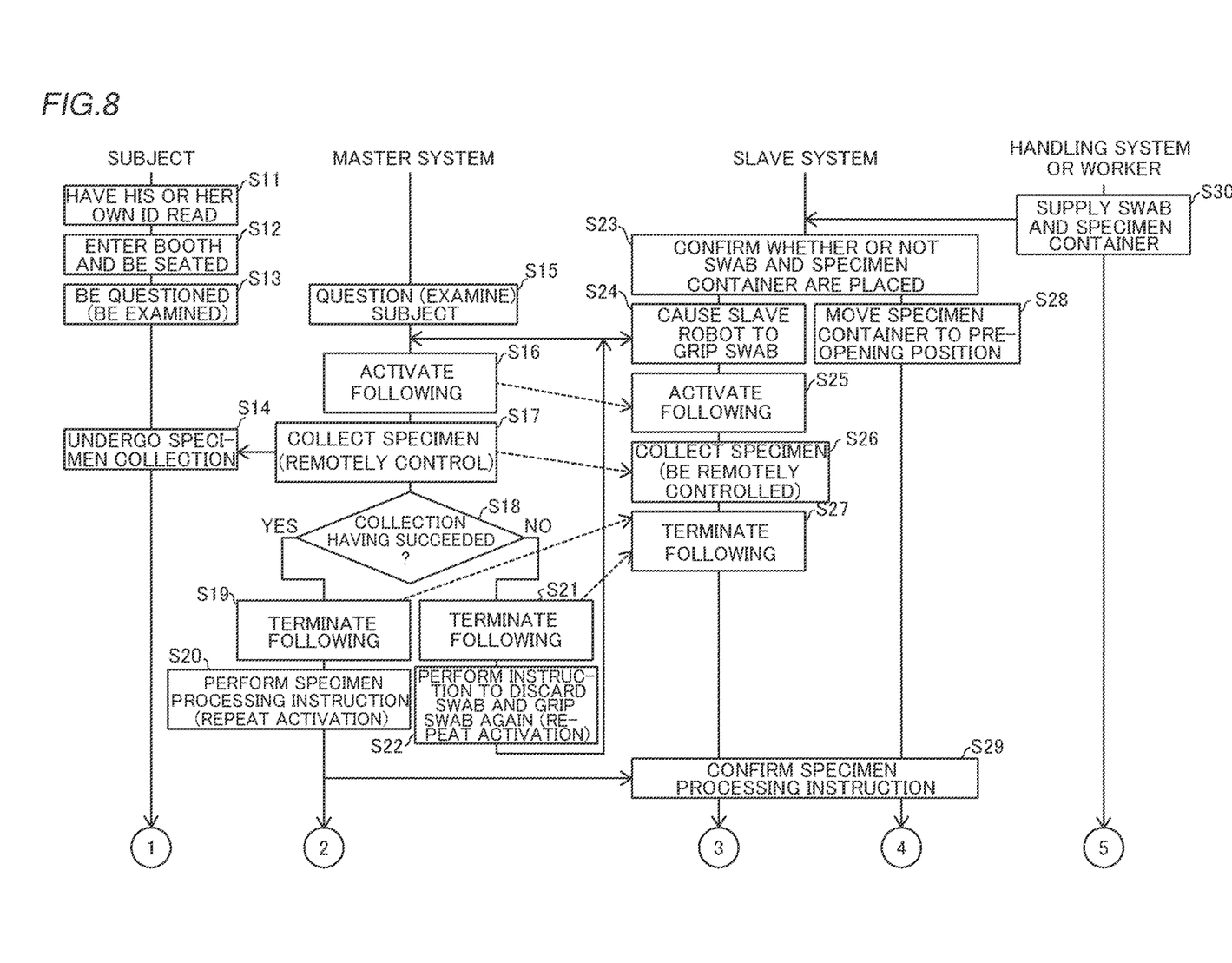
FIG. 8 is a first flowchart for illustrating the procedure of the specimen collection process of the robot system according to the embodiment.

In step S11 of FIG. 8, the subject S has his or her own ID (identification) read. In step S12, the subject S enters the booth 10 and is seated.

The handling robot 40 of the handling system or the worker supplies the specimen collection member 12a (swab) and the specimen container 12b to the supply position 13a in step S30. In step S23, the slave system confirms whether or not the specimen collection member 12a (swab) and the specimen container 12b are placed at the supply position 13a. Specifically, the object detector 13 confirms that the specimen collection member 12a (swab) and the specimen container 12b are placed.

In step S13 and step S15, the operation person O questions the subject S. Specifically, through the camera and the display 25, the operation person O talks with the subject S over the phone and questions the subject S.

When the questionnaire is completed, in the slave system, the slave robot 11 grips the specimen collection member 12a (swab) in step S24. Furthermore, in step S28, the specimen container 12b is moved to a pre-opening position.

In the master system, a following is activated in step S16. Furthermore, in the slave system, the following of the slave robot 11 is activated in step S25. Thus, the master robot 20 can remotely control the slave robot 11.

In step S14, step S17, and step S26, the slave robot 11 is remotely controlled by the master robot 20 to collect a specimen from the subject S. In step S18, the operation person O determines whether or not the specimen collection has succeeded. When the specimen collection has succeeded, the following is terminated in step S19. Thus, in the slave system, the following is terminated in step S27. Consequently, the master robot 20 is no longer able to remotely control the slave robot 11.

In the master system, a specimen processing instruction (repeat activation) is performed in step S20. Thus, in the slave system, the specimen processing instruction is confirmed in step S29.

When the specimen collection has not succeeded in step S18, the following is terminated in step S21. Thus, in the slave system, the following is terminated in step S27, and the master robot 20 is no longer able to remotely control the slave robot 11. In step S22, an instruction to discard the specimen collection member 12a (swab) and grip the specimen collection member 12a (swab) again (repeat activation) is performed. After that, the process returns to step S16, and the specimen collection procedure is performed again.

Figure 9:
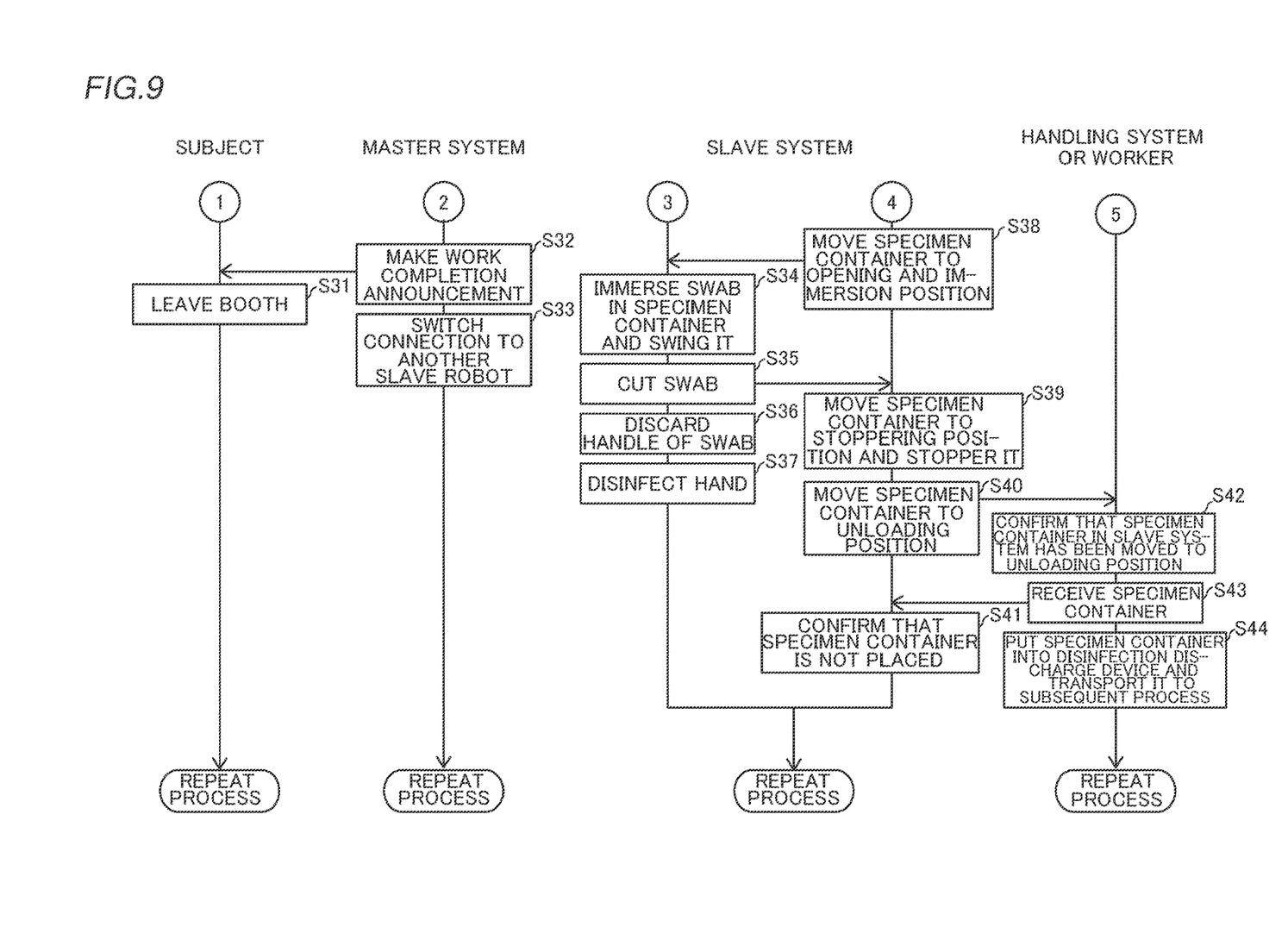
FIG. 9 is a second flowchart for illustrating the procedure of the specimen collection process of the robot system according to the embodiment.

When the specimen collection is completed, the master system makes a work completion announcement to the subject S in step S32 of FIG. 9. Specifically, the operation person O informs the subject S that the specimen collection has been completed. In step S31, the subject S whose specimen collection has been complected leaves the booth 10.

In the master system, the operation person O switches the connection to another slave robot 11 in step S33.

In the slave system, the specimen container 12b is moved to an opening and immersion position in step S38. In step S34, the slave robot 11 immerses the specimen collection member 12a (swab) in the specimen container 12b and swings it. In step S35, a tip end of the specimen collection member 12a (swab) is cut by a swab cutting device, and the cut tip end is stored in the specimen container 12b.

In step S39, the specimen container 12b is moved to a stoppering position and stoppered. In step S40, the specimen container 12b is moved to the unloading position 14a.

In step S36, the handle of the specimen collection member 12a (swab) is discarded. Furthermore, in step S37, the hand 12 at the tip end of the slave robot 11 is disinfected.

In step S42, the handling robot 40 of the handling system or the worker confirms that the specimen container 12b in the slave system has been moved to the unloading position 14a. Specifically, the unloading detector 14 confirms that the specimen container 12b is placed at the unloading position 14a. In step S43, the handling robot 40 of the handling system or the worker receives the specimen container 12b from the unloading position 14a.

In step S41, the slave system confirms that the specimen container 12b is not placed at the unloading position 14a. In step S44, the handling robot 40 of the handling system or the worker puts the specimen container 12b into a disinfection discharge device and transports it to a subsequent process. Thereafter, the specimen collection process is repeated using the same procedure.

Advantages of this Embodiment

According to this embodiment, the following advantages are achieved.

According to this embodiment, as described above, the robot system 100 includes the master robot 20 and the plurality of slave robots 11 remotely controlled by the master robot 20 to collect a specimen from the subject S. Accordingly, the operation person O who operates the master robot 20 does not need to be positioned close to the subject S, and thus the risk of infection from the subject S to the operation person O can be reduced. Furthermore, the plurality of slave robots 11 can be remotely controlled by one master robot 20 while the plurality of slave robots 11 are switched, and thus after a specimen is collected by one slave robot 11, a specimen can be collected from another subject S using another slave robot 11 while the booth 10 in which the specimen has been collected is disinfected to prevent infection or while a subject S is on standby in the booth 10. Consequently, the number of specimens collected per unit time can be increased. Furthermore, it is not necessary to provide a master robot 20 for each slave robot 11, and thus the number of master robots 20 provided can be reduced. Thus, the system configuration can be simplified, and an increase in the size of the installation space can be reduced or prevented.

According to this embodiment, as described above, the robot system 100 includes the selection operator 24 on the master robot 20 side to select the slave robot 11 to be remotely controlled from among the plurality of slave robots 11. Accordingly, the slave robot 11 to be remotely controlled can be easily selected from among the plurality of slave robots 11 by operating the selection operator 24.

According to this embodiment, as described above, the switching controller 30 is configured or programmed to acquire whether or not the slave robot 11 selected by the selection operator 24 is moving, and switch the operational connection such that the selected slave robot 11 is remotely controlled by the master robot 20 when the selected slave robot 11 is remotely controllable. Accordingly, when the slave robot 11 is moving for disinfection, for example, the operational connection is not switched for remote control, and thus interruption of the process of the slave robot 11 for disinfection, for example, can be reduced or prevented.

According to this embodiment, as described above, the switching controller 30 is configured or programmed to receive an operation signal to perform a remote control from the master robot 20, and transmit a movement command signal based on the operation signal to the slave robot 11 to be remotely controlled. Accordingly, the slave robot 11 can be remotely controlled by the master robot 20 via the switching controller 30, and thus the slave robot 11 to be remotely controlled by the master robot 20 can be easily switched to one slave robot 11 by switching of the operational connection by the switching controller 30.

According to this embodiment, as described above, the robot system 100 includes the object detector 13 to detect that the object including the specimen collection member 12a collecting a specimen and the specimen container 12b in which the specimen is to be stored has been placed at the supply position 13a at which the object is supplied to the slave robot 11. Furthermore, the slave robot 11 becomes remotely controllable for specimen collection when the object detector 13 detects that the object has been supplied to the supply position 13a. Accordingly, it is not necessary to change the mechanical configuration and control configuration of the slave robot 11 depending on whether the handling robot 40 supplies the object to the slave robot 11 or the worker supplies the object to the slave robot 11. Thus, an accessory structure for supplying the object can be easily provided for the slave robot 11.

According to this embodiment, as described above, the robot system 100 includes the unloading detector 14 to detect that the specimen container 12b in which the collected specimen has been stored has been placed at the unloading position 14a. Furthermore, the slave robot 11 becomes remotely controllable for specimen collection when the unloading detector 14 detects that the specimen container 12b has been unloaded from the unloading position 14a. Accordingly, it is not necessary to change the mechanical configuration and control configuration of the slave robot 11 depending on whether the handling robot 40 unloads the specimen container 12b from the unloading position 14a or the worker unloads the specimen container 12b from the unloading position 14a. Thus, an accessory structure for unloading the specimen container 12b can be easily provided for the slave robot 11.

According to this embodiment, as described above, the robot system 100 includes the handling robot 40 to supply the object to the supply position 13a and unload the specimen container 12b in which the collected specimen has been stored from the unloading position 14a. Furthermore, the handling robot 40 is operable to acquire the position of the slave robot 11 to supply the object and unload the specimen container 12b. Accordingly, the position of the slave robot 11 is unilaterally acquired by the handling system such that the handling robot 40 can be moved without interfering with the slave robot 11. Thus, the handling robot 40 can be provided for the slave robot 11 without changing the mechanical configuration and control configuration of the slave robot 11.

According to this embodiment, as described above, the robot system 100 includes the movement detector 15 to detect movement of the handling robot 40 to the supply position 13a and the unloading position 14a. Furthermore, the slave robot 11 is operable to acquire the object from the supply position 13a when the movement detector 15 does not detect the handling robot 40. Moreover, the slave robot 11 is operable to place the specimen container 12b at the unloading position 14a when the movement detector 15 does not detect the handling robot 40. Accordingly, the movement detector 15 can detect the handling robot 40 when the handling robot 40 is provided and can detect the worker when the handling robot 40 is not provided, and thus it is not necessary to change the mechanical configuration and control configuration of the slave robot 11 depending on whether the handling robot 40 is provided or work is performed by the worker without providing the handling robot 40.

According to this embodiment, as described above, the handling robot 40 is provided in common for the plurality of slave robots 11. Accordingly, an increase in the number of handling robots 40 can be reduced or prevented, and thus the complexity of the device configuration can be reduced or prevented.

According to this embodiment, as described above, the handling robot 40 is arranged between the two slave robots 11 and is provided in common for the two slave robots 11. Accordingly, one handling robot 40 can easily supply the objects to the two slave robots 11 and unload the specimen containers 12b.

According to this embodiment, as described above, the slave robot 11 is operable to insert the specimen collection member 12a from the nostril of the subject S to collect the specimen. Accordingly, even when the subject S coughs or sneezes due to inserting the specimen collection member 12a from the nasal cavity, contact of the operation person O with the droplets can be reduced or prevented, and thus the risk of infection to the operation person O can be effectively reduced.

MODIFIED EXAMPLES

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while the example in which the robot system is used to collect a specimen from the person to be treated by remote control has been shown in the aforementioned embodiment, the present disclosure is not limited to this. In the present disclosure, the operation person may perform a procedure other than specimen collection on the person to be treated by remote control using the robot system. The robot system may be used to perform an examination on the person to be treated, for example.

Figure 10:
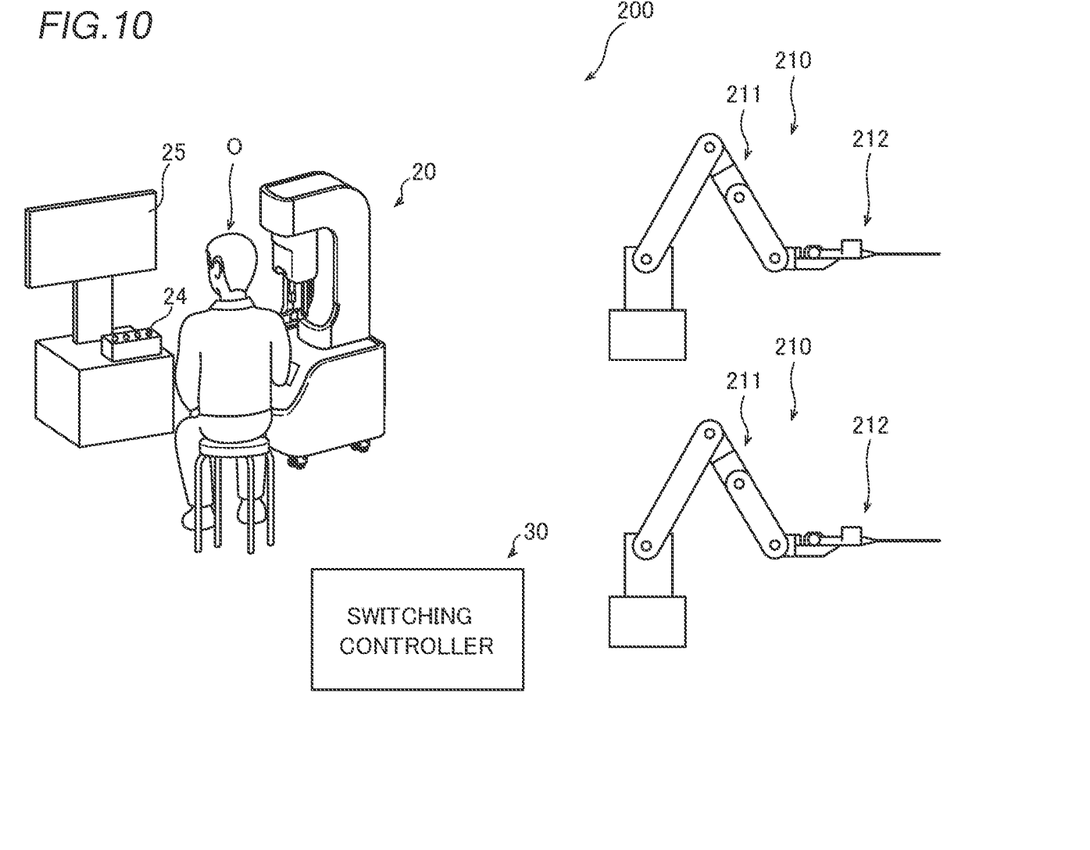
FIG. 10 is a diagram schematically showing a robot system according to a modified example of the embodiment.
Figure 11:
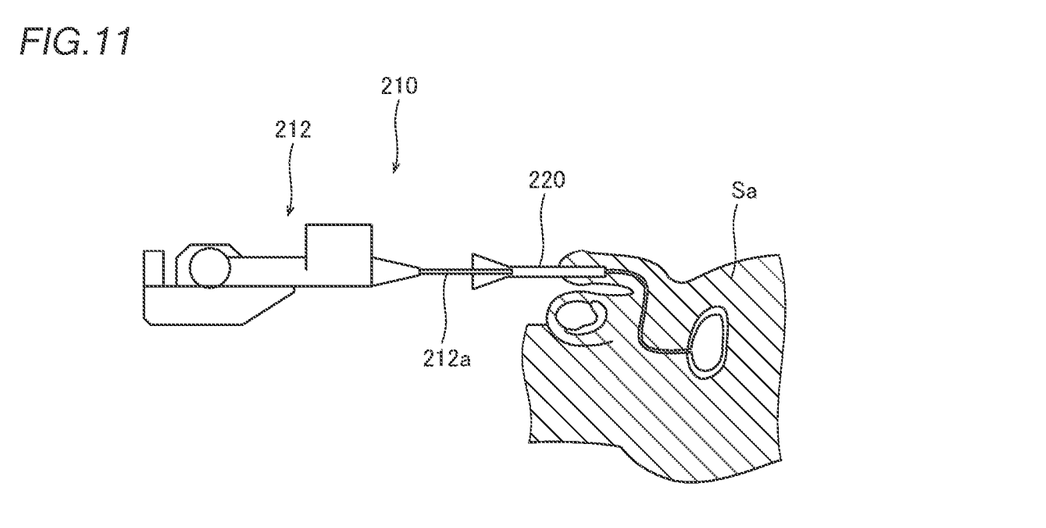
FIG. 11 is a diagram for illustrating an example of a procedure performed by the robot system according to the modified example of the embodiment.

Specifically, as shown in FIGS. 10 and 11, an endoscope such as a ureteroscope may be inserted into the person to be treated Sa, and a procedure such as examination and treatment may be performed. In an example of a robot system 200 shown in FIG. 10, an operation person O operates slave robots 210 using a master robot 20. Each of the slave robots 210 includes a robot arm 211 and a treatment member 212, such as a ureteroscope, provided at a tip end of the robot arm 211. As shown in FIG. 11, a tip end 212a of the treatment member 212 including an imager and a treatment portion is inserted into the ureter through a ureteral access sheath 220 inserted into the urethral opening. Furthermore, the position and posture of the treatment member 212 are changed by the robot arm 211. Thus, the operation person O can perform the procedure on the person to be treated Sa by remote control. An image captured by the imager provided at the tip end 212a is displayed on a display 25 arranged on the master robot 20 side.

While the example in which the slave robot is a vertical articulated robot has been shown in the aforementioned embodiment, the present disclosure is not limited to this. In the present disclosure, the slave robot may be a robot other than a vertical articulated robot such as a horizontal articulated robot and/or a dual-arm robot.

While the example in which four slave robots are provided for one master robot has been shown in the aforementioned embodiment, the present disclosure is not limited to this. In the present disclosure, two, three, or five or more slave robots may be provided for one master robot.

While the example in which one handling robot is provided in common for two slave robots has been shown in the aforementioned embodiment, the present disclosure is not limited to this. In the present disclosure, one handling robot may be provided for each slave robot, or one handling robot may be provided in common for three slave robots.

While the process operations of the controllers are described using a flow in a flow-driven manner in which processes are performed in order along a process flow for the convenience of illustration in the aforementioned embodiment, the present disclosure is not limited to this. In the present disclosure, the process operations of the controllers may be performed in an event-driven manner in which the processes are performed on an event basis. In this case, the process operations may be performed in a complete event-driven manner or in a combination of an event-driven manner and a flow-driven manner.

DESCRIPTION OF REFERENCE NUMERALS

11: slave robot
20: master robot
24: selection operator
30: switching controller
100: robot system
S: subject (person to be treated)

The invention claimed is:

1. A robot system comprising:
a master robot controller;
a plurality of slave robots remotely controlled by the master robot controller to perform a medical procedure on a person to be treated, each of the plurality of slave robots remotely controllable by the master robot controller when stopped; and not remotely controllable by the master robot controller when moving for pre-processing or post-processing; and
a switching controller configured or programmed to perform operations comprising operations to:
switch an operational connection between the master robot controller and each of the plurality of slave robots such that each of the plurality of slave robots is remotely controlled by the master robot controller when the respective slave robot is stopped in a waiting state thereof after independently moving for performing pre-processing operations and before independently moving for performing post-processing operations by the respective slave robot; wherein
the switching controller is configured or programmed to, in response to receiving an operation to select a slave robot of the plurality of slave robots for remote control, acquire whether or not the slave robot selected to be remotely controlled from among the plurality of slave robots is moving, and switch the operational connection such that a selected slave robot is remotely controlled by the master robot controller when the selected slave robot is stopped.

2. The robot system according to claim 1, further comprising:
a selection operator that receives the operation to select the slave robot to be remotely controlled from among the plurality of slave robots.

3. The robot system according to claim 1, wherein the switching controller is configured or programmed to receive an operation signal to perform a remote control from the master robot controller, and transmit a movement command signal based on the operation signal to the slave robot to be remotely controlled among the plurality of slave robots.

4. The robot system according to claim 1, wherein
the medical procedure comprises collecting a specimen from on the person to be treated, and
the pre-processing operations comprise
confirming whether or not a specimen collection member and a specimen container for collecting the specimen are placed at a supply position for performing the medical procedure, and
gripping at least the specimen collecting member.

5. The robot system according to claim 1, wherein
the medical procedure comprises collecting a specimen from on the person to be treated, and
the post-processing operations comprise
confirming a processing instruction for processing the collected specimen, and
processing the collected specimen according to the confirmed processing instruction.

* * * * *